US011740245B2

(12) United States Patent
García Giménez et al.

(10) Patent No.: US 11,740,245 B2
(45) Date of Patent: Aug. 29, 2023

(54) MASS SPECTROMETRY-BASED METHODS FOR THE DETECTION OF CIRCULATING HISTONES H3 AND H2B IN PLASMA FROM SEPSIS OR SEPTIC SHOCK (SS) PATIENTS

(71) Applicants: Centro de Investigación Biomédica en Red (CIBER-ISCIII), Madrid (ES); Fundación INCLIVA, Valencia (ES); Universitat de València Estudi General, Valencia (ES)

(72) Inventors: José Luis García Giménez, Valencia (ES); Carlos Romá Mateo, Valencia (ES); Federico V. Pallardó Calatayud, Valencia (ES)

(73) Assignees: Centro de Investigación Biomédica en Red (CIBER-ISCIII), Madrid (ES); Fundación INCLIVA, Valencia (ES); Universitat de Valencia Estudi General, Valencia (ES)

( * ) Notice: Subject to any disclaimer, the term of this patent is extended or adjusted under 35 U.S.C. 154(b) by 829 days.

(21) Appl. No.: 16/346,978

(22) PCT Filed: Nov. 6, 2017

(86) PCT No.: PCT/EP2017/078362
§ 371 (c)(1),
(2) Date: May 2, 2019

(87) PCT Pub. No.: WO2018/083308
PCT Pub. Date: May 11, 2018

(65) Prior Publication Data
US 2020/0264190 A1 Aug. 20, 2020

(30) Foreign Application Priority Data
Nov. 4, 2016 (EP) .................................... 16382509

(51) Int. Cl.
*G01N 33/68* (2006.01)
(52) U.S. Cl.
CPC ..... *G01N 33/6848* (2013.01); *G01N 33/6893* (2013.01); *G01N 2800/26* (2013.01); *G01N 2800/56* (2013.01)

(58) Field of Classification Search
CPC .......... G01N 33/6848; G01N 2800/26; G01N 2800/56
See application file for complete search history.

(56) References Cited

U.S. PATENT DOCUMENTS

| 7,645,613 B2 * | 1/2010 | Ivey | G01N 33/6848 436/173 |
| 2010/0292131 A1 * | 11/2010 | Kas | G01N 33/6893 435/7.92 |

FOREIGN PATENT DOCUMENTS

| JP | 2011-503012 A | 1/2011 |
| JP | 2014-516511 A | 7/2014 |
| WO | 2004/044555 A2 | 5/2004 |
| WO | 2012/106396 A2 | 8/2012 |
| WO | 2013/148178 A1 | 10/2013 |
| WO | 2013/191280 A1 | 12/2013 |
| WO | WO-2016128383 A1 * | 8/2016 | ......... G01N 33/6875 |

OTHER PUBLICATIONS

Promega. "Trypsin/Lys-C protease mix for enhanced protein mass spectrometry analysis." Nature Methods (2013) i-ii. (Year: 2013).*
Beck et al., "Quantitative Proteomic Analysis of Post-translational Modifications of Human Histones," *Molecular & Cellular Proteomics* 5(7):1314-1325, 2006.
García-Giménez et al., "A new mass spectrometry-based method for the quantification of histones in plasma from septic shock patients," *Scientific Reports* 7(10643):1-10, 2017.
Li et al., "Identification of citrullinated histone H3 as a potential serum protein biomarker in a lethal model of lipopolysaccharide-induced shock," *Surgery* 150(3):442-451, 2011.
Xu et al., "Extracellular histones are major mediators of death in sepsis," *Nature Medicine* 15(11):1318-1322, 2009.

* cited by examiner

*Primary Examiner* — Christopher Adam Hixson
(74) *Attorney, Agent, or Firm* — SEED INTELLECTUAL PROPERTY LAW GROUP LLP

(57) ABSTRACT

The present invention proposes a novel method for the detection of circulating histones H3 and H2B in plasma from sepsis or septic shock (SS) patients, based on mass spectrometry-based methods, in particular based on multiple reaction monitoring targeted mass spectrometry (MRM-MS). Such methods allow quantification of histones using an internal standard and show strong specificity and sensitivity values.

4 Claims, 10 Drawing Sheets

Specification includes a Sequence Listing.

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial Sequence
<220> FEATURE:
<223> OTHER INFORMATION: STELLIR peptide (H3)

<400> SEQUENCE: 1

Ser Thr Glu Leu Leu Ile Arg
1               5

<210> SEQ ID NO 2
<211> LENGTH: 9
<212> TYPE: PRT
<213> ORGANISM: Artificial Sequence
<220> FEATURE:
<223> OTHER INFORMATION: LLLPGELAK peptide (H2B)

<400> SEQUENCE: 2

Leu Leu Leu Pro Gly Glu Leu Ala Lys
1               5
```

MASS SPECTROMETRY-BASED METHODS FOR THE DETECTION OF CIRCULATING HISTONES H3 AND H2B IN PLASMA FROM SEPSIS OR SEPTIC SHOCK (SS) PATIENTS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200290_401USPC_SEQUENCE_LISTING.txt. The text file is 4 KB, was created on Feb. 21, 2020, and is being submitted electronically via EFS-Web. The attached text file Sequence Listing is identical to the Sequence Listing filed during the International Phase.

FIELD OF THE INVENTION

The present invention is related to the medical field, in particular to the field of diagnosis/prognosis of disease based on the detection of plasma biomarkers by using mass spectrometry-based methods. More particularly, the present invention is related to mass spectrometry-based methods for the detection of circulating histones H3 and H2B in plasma patients suspected of suffering from sepsis or septic shock for the diagnosis/prognosis of sepsis or septic shock in those patients.

BACKGROUND OF THE INVENTION

Sepsis is defined as the host systemic inflammatory response to severe, life-threatening infection, with the presence of biochemical abnormalities and organ dysfunction. It is a major healthcare problem, affecting millions of people around the world every year. Its incidence is increasing owing to the ageing population, immuno-senescence, and the resulting impaired immunity. Moreover, it is the most frequent cause of mortality in most intensive care units (ICUs), especially if not recognized and treated promptly. Despite its worldwide importance and being considered a public health concern, accounting for more than $20 billion (5.2%) of total US hospital costs in 2011, public awareness of sepsis is poor.

Septic shock should be defined as a subset of sepsis in which particularly profound circulatory, cellular, and metabolic abnormalities are associated with a greater risk of mortality than with sepsis alone. Patients with septic shock can be clinically identified by a vasopressor requirement to maintain a mean arterial pressure of 65 mm Hg or greater and serum lactate level greater than 2 mmol/L (>18 mg/dL) despite adequate volume resuscitation.

The short-term mortality of sepsis ranges between 10-40% and has been reported to be as high as 30-60% in septic shock. Early goal-directed therapy and appropriate antibiotic treatment given to the patient as early as possible have both proved effective in reducing mortality, but despite the improvements in treatment, short-term mortality is still very high.

The presence of circulating histones in relation to septic processes has been studied previously, and several works show a direct correlation between the presence of specific histones in plasma and the symptoms derived from prolonged sepsis. Circulating histones are found in the blood of healthy individuals at low concentrations, but their levels increase largely in patients suffering from severe trauma, systemic inflammation, sepsis or tissue damage. Noteworthy, histone proteins show an interesting cytotoxic potential, which has been demonstrated to affect bacterial and mammalian cells, contributing to worsen sepsis evolution.

However, no definitive consensus has been reached regarding the specific concentration levels for each histone type in relation to their pathogenicity. In addition, the specific histone levels and their capacity to be used to monitor sepsis progression as well as the correlation with the effectiveness of treatments, have never been fully elucidated. This is due, in the vast majority of cases, due to the lack of specific and sensitive methods to analyze the presence and, moreover, to quantify the levels of circulating histones.

Immunoassays (IAs) for detection of free histone proteins circulating in plasma have been used previously, but the results obtained by IAs show low reproducibility, high error ranges, and low sensitivity. In addition, semi-quantitative IAs show many flaws, such as poor concordance between assays, differences in reproducibility when using different kits from manufactures which use different proprietary antibodies (recognizing different epitopes in each assay), and variable cross-reactivity. Furthermore, a variety of interferences can occur in IAs, including anti-reagent antibodies and endogenous autoantibodies present in the assayed biological samples, which can generate erroneous results and cause clinical side effects.

Therefore, there is a need for the replacement of the current IAs by other methods or techniques which increased the sensitivity and specificity of the detection of diagnostic and prognostic sepsis biomarkers.

BRIEF DESCRIPTION OF THE INVENTION

The authors of the present invention have come to the conclusion that by replacing the current IA methods by mass spectrometry-based methods there is a significant improvement in the sensitivity and specificity of the detection of biomarkers linked to sepsis' diagnosis and prognosis. In this regard, targeted mass spectrometry (MS) using specific heavily labeled Spike-In peptides is shown herein as an efficient and sensitive approach for blood circulating histones identification and quantification. Hence, by using said mass spectrometry-based methods, monitoring of sepsis and/or septic shock will largely benefit from new, affordable biomarkers with high sensitivity, and specificity.

In this sense, in the present invention, we propose a novel method for the detection of circulating histones H3 and H2B in plasma from sepsis or septic shock (SS) patients, based on mass spectrometry-based methods, in particular based on multiple reaction monitoring targeted mass spectrometry (MRM-MS) and multiple reaction monitoring approach. Such methods allow quantification of histones using an internal standard and show strong specificity and sensitivity values. Using biological samples from patients, as compared to healthy controls, we have further validated our method and, moreover, we have been able to set a threshold for the plasma histone levels that correlate with a fatal outcome for septic shock patients. The method could thus set the standard for the implantation of mass-spectrometry based quantification of histone H3 and H2B levels in pathologies with presence of these circulating histones, providing a most valuable tool to monitor disease progression and clinical interventions.

DETAILED DESCRIPTION OF THE INVENTION

Figure 1:
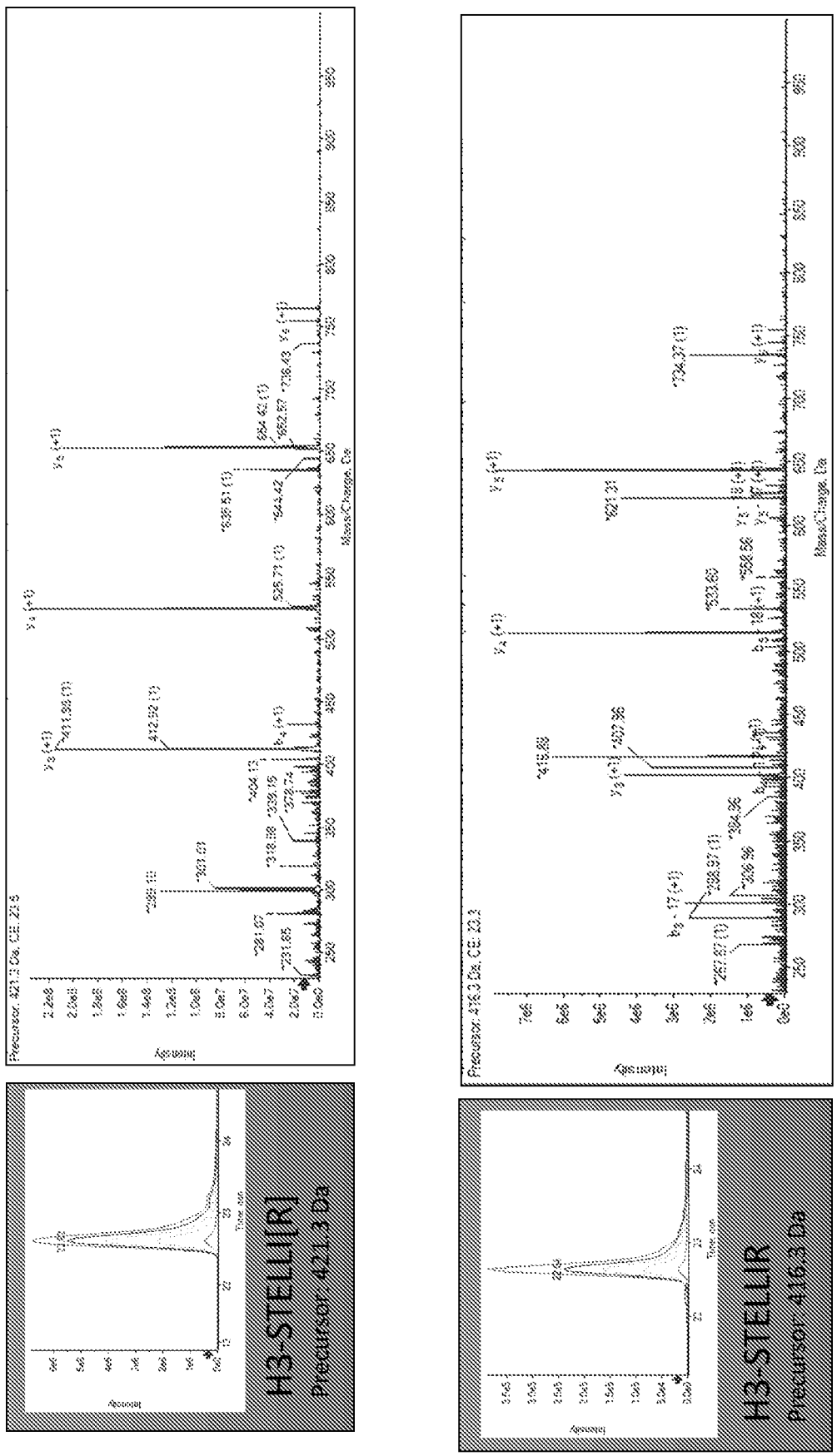
FIG. 1. Overview of targeted protein quantitation of histone H2B and H3 by MRM-MS. Chromatograms for peptides LLLPGELAK and STELLIR showing the integrated peak areas from the signal corresponding to transitions (heavy, 300 fmol and endogen). Peak areas for targeted peptides are compared to those for stable Spike-In peptides used as standards. Sequence-specific transitions derived from the MS/MS spectrum are also shown.
Figure 1:
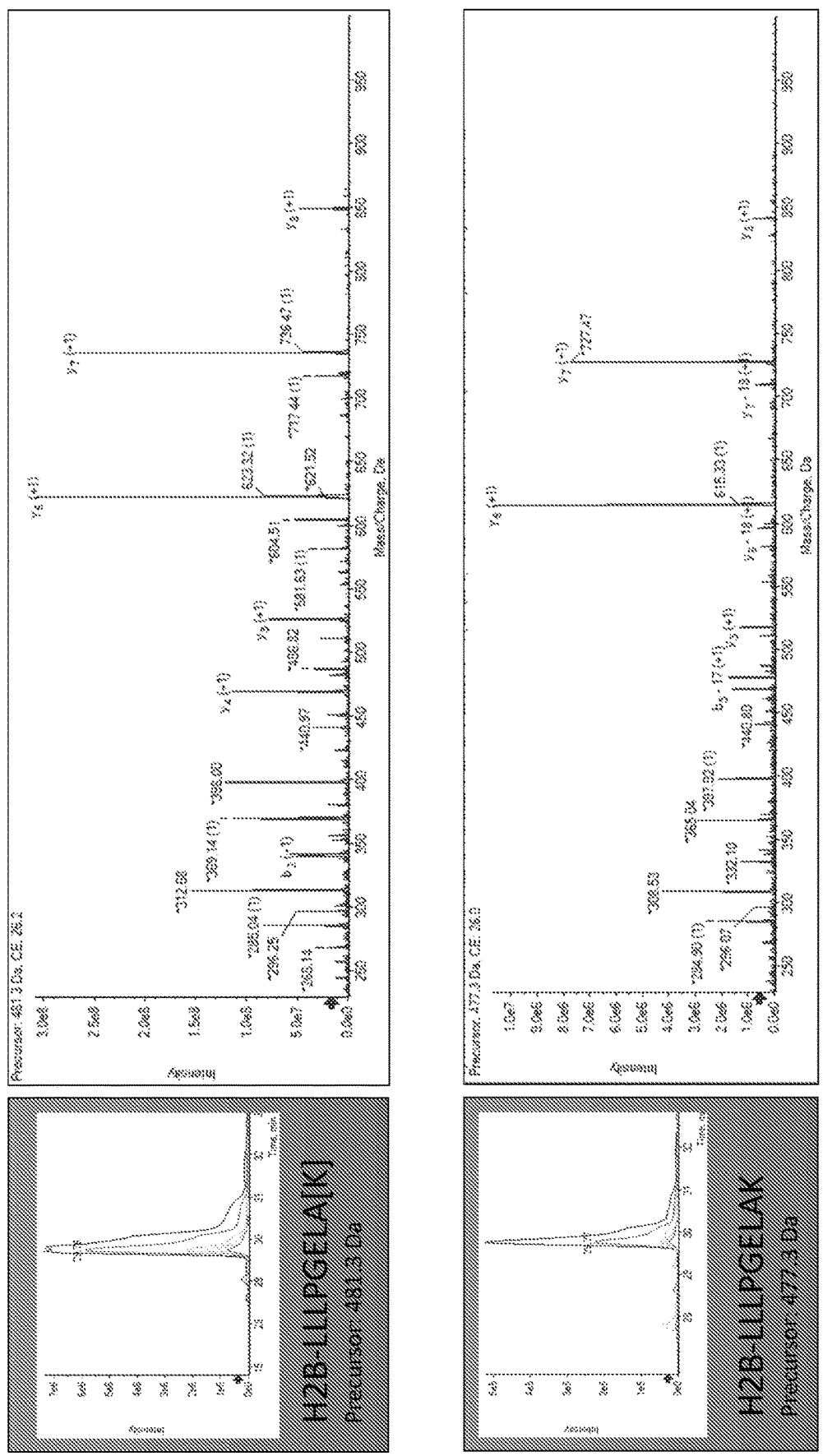

Early diagnosis and rapid patient stratification of sepsis and SS may improve patient outcome by redefining the specific treatment in a timely and proper manner. This is a challenge for ICU's practitioners who require new biomarkers for recognizing patients susceptible to progress towards a more critical pathological condition. The complexities of the pathophysiology of sepsis and SS and their many nosological threats, are the reasons why neither clinical nor biological biomarkers have proven to be highly accurate to predict adverse outcomes.

MRM-MS offers a potential methodology for both biomarker discovery and biomarker validation. In addition, this method provides the sensitivity, accuracy and high throughput needed for clinical validation of biomarkers, thus eliminating the necessity of performing different discovery and validation methods. Plasma is a source of biomarkers for diagnostic assays, but it is also a challenging biological matrix for proteomic studies because of the wide dynamic range of proteins present in this fluid ($10^{10}$). Monitoring of a single transition per peptide has been proposed as being sufficiently specific for peptide quantitation in complex mixtures such as plasma. On the other hand, classical biomarkers do not add more information than generic scores in predicting outcome in septic patients. Despite having CRP and PCT to complement the diagnosis of sepsis, and the usefulness of the PCT as a prognostic biomarker, the future knowledge of sepsis requires finding of new biomarkers that can be sensitive, specific, and economically affordable.

The overwhelming immune response to infection can release histones into the blood not only to fight infection by a process called NETosis, but also as a consequence of endothelial damage and apoptosis of neutrophils and other immune cells. Toxicity for all histone types has been described, but some data are controversial in this regard, including histone type and plasma concentration. Abrams and collaborators obtained similar cytotoxicity results for both inter-linker histone H1 and core H2A, H2B, H3 and H4 histones, whilst other authors found higher cytotoxicity for H3, H4 and in some cases H2B, rather than H2A. Furthermore, histones mediate apoptosis of cells in the lymphoid compartment including the thymus, spleen, and blood. Particularly, H4 has been proposed as the main histone driving lymphocyte apoptosis. Other studies have identified histone H3 and nucleosomes in plasma from septic patients.

Besides histone type, IAs have provided different levels of circulating histones in sepsis, but previous studies were never able to give a tight range of concentrations which could be considered as cytotoxic. In order to identify a sensitive and specific method to quantify circulating histones in plasma samples we develop a MRM-MS based method which uses LLLPGELAK and STELLIR Spiked-In peptides to detect H2B and H3 histones, respectively.

The present method permits the identification of patients with significant correlation coefficients in both survivors and non-survivors to the septic episode within the first 24 hours at ICU. The presence of both histones could be used for clinical purposes, establishing for the first time a specific concentration range of plasma histones H2B and H3 to be used as first triage criteria when patients arrive to ICU and also become valuable prognostic biomarker of septic shock fatal outcome.

In order to provide for such methodology and select the best peptides having significant correlation coefficients in both survivors and non-survivors to the septic episode within the first 24 hours at ICU, we performed an analysis by nano-LCMSMS-DIA using a 5600 TripleTOF mass spectrometer (SCIEX) of H2B_HUMAN and H3_HUMAN proteins, pure standards. Such analysis allowed us to identify by BLAST a total of 29 tryptic peptides for H2B_HUMAN with a statistical confidence of 95% or higher. In the case of H3_HUMAN this analysis allow us to assign 18 peptides, with statistical confidence of 95% or higher.

In addition, by using bioinformatic programs MRM Pilot (Sciex) and Skyline (Macoss Lab, Department of Genome Sciences, UW, USA), and discarding those peptides which had missed cleavages and amino acids susceptible to modification (M/W/Q/N), the list of candidates suitable for use in downstream MRM experiments was reduced to:

| H2B_HUMAN | H3_HUMAN |
|---|---|
| ESYSVYVYK | STELLIR |
| LLLPGELAK | YRPGTVALR |

Figure 6:
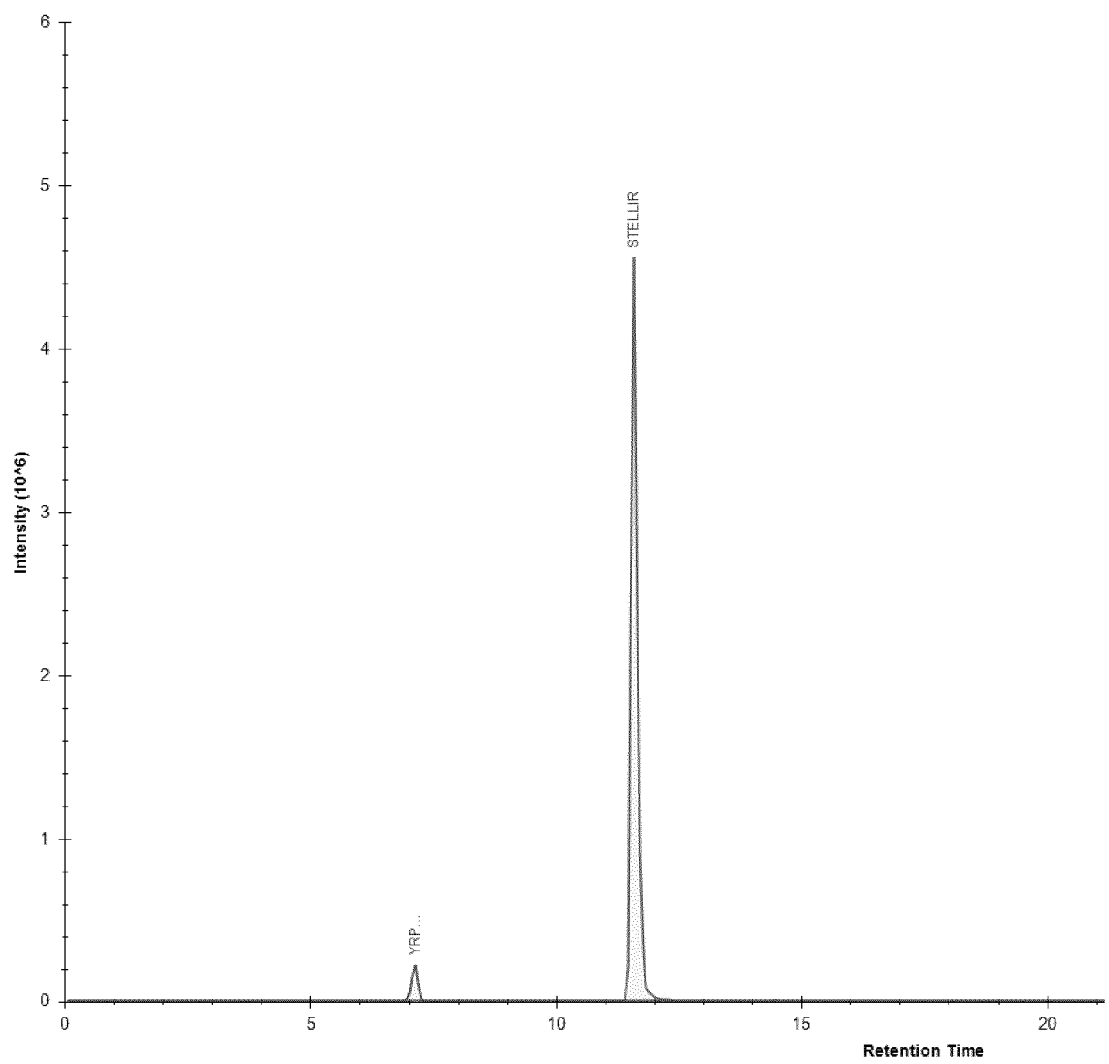
FIG. 6. Intensity in the nano-LC-MRM-MS chromatograms for STLLIR in pure standard protein H3.1
Figure 7:
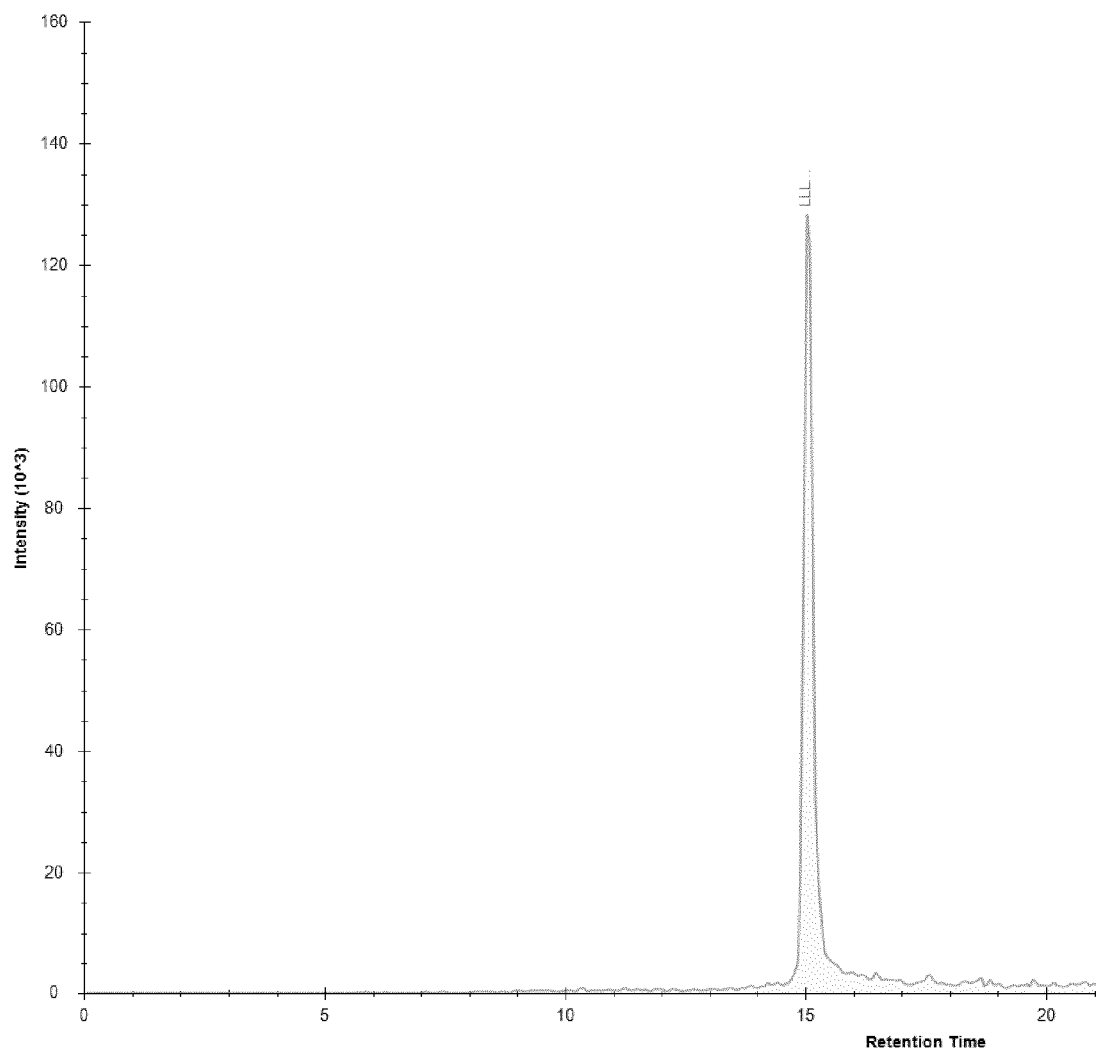
FIG. 7. Intensity in the nano-LC-MRM-MS chromatograms for LLLPGELAK in pure standard protein H2B.

In the process of tuning the acquisition parameters such as 'Declustering Potential' and 'Collision Energy' and during the analysis of the standard proteins in complex matrices, it was determined that the most intense peptides were STELLIR for H3.1 and LLLPGELAK for H2B, so they were chosen as candidates for MRM-MS experiments for circulating histone H3 and H2B quantitation. The difference in intensity is illustrated in the nanoLC-MRM-MS chromatograms shown in FIGS. 6 and 7 for each pure standard protein.

Figure 8:
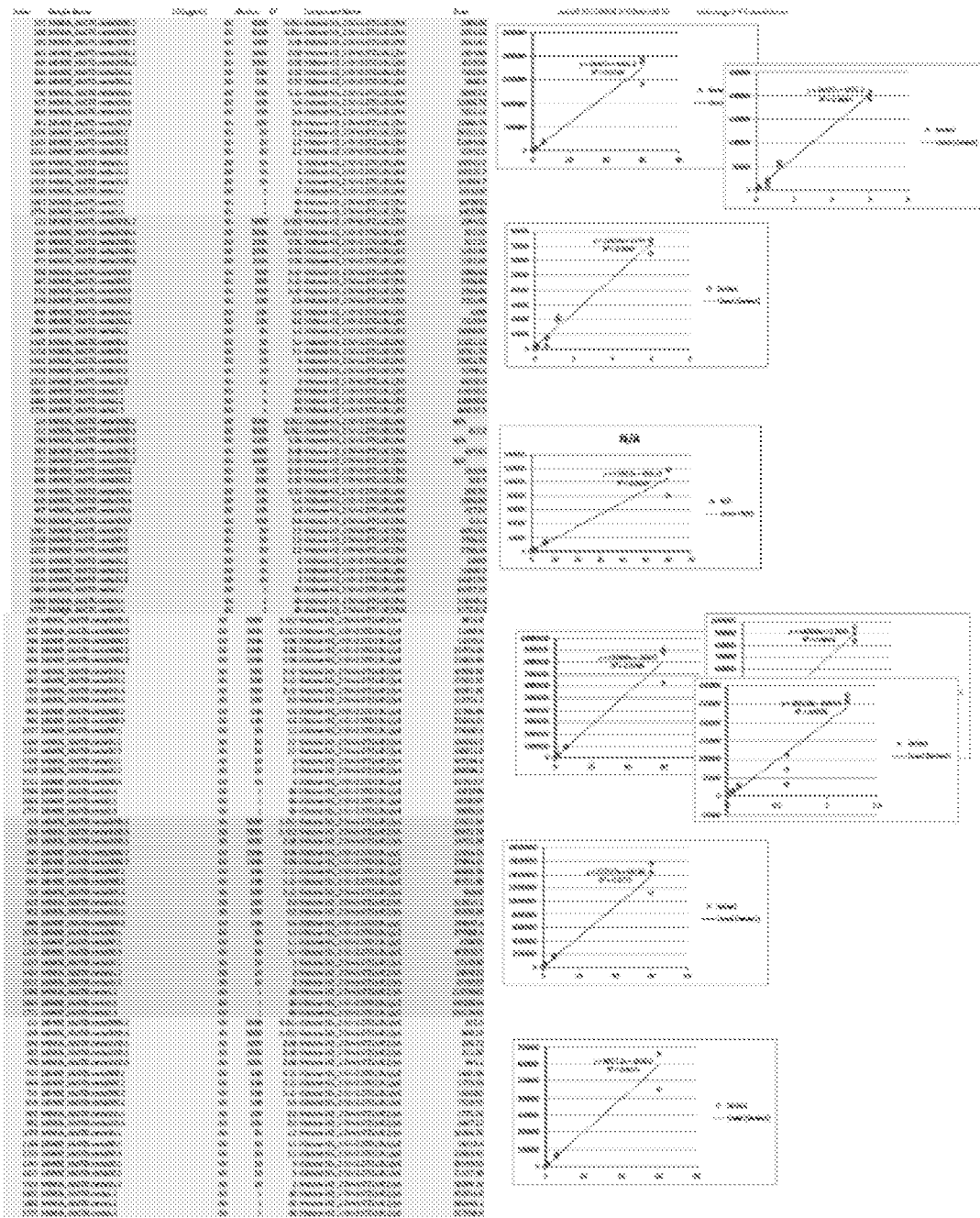
FIG. 8. Response curves for peptide LLLPGELAK for histone H2B. The concentration of light peptide was varied between 0.012 ug/mL to 60 ug/mL and measured relative to the heavy peptide signal. The graphs show the linear regression between area form MS spectrum to peptide concentration for different transitions.
Figure 9:
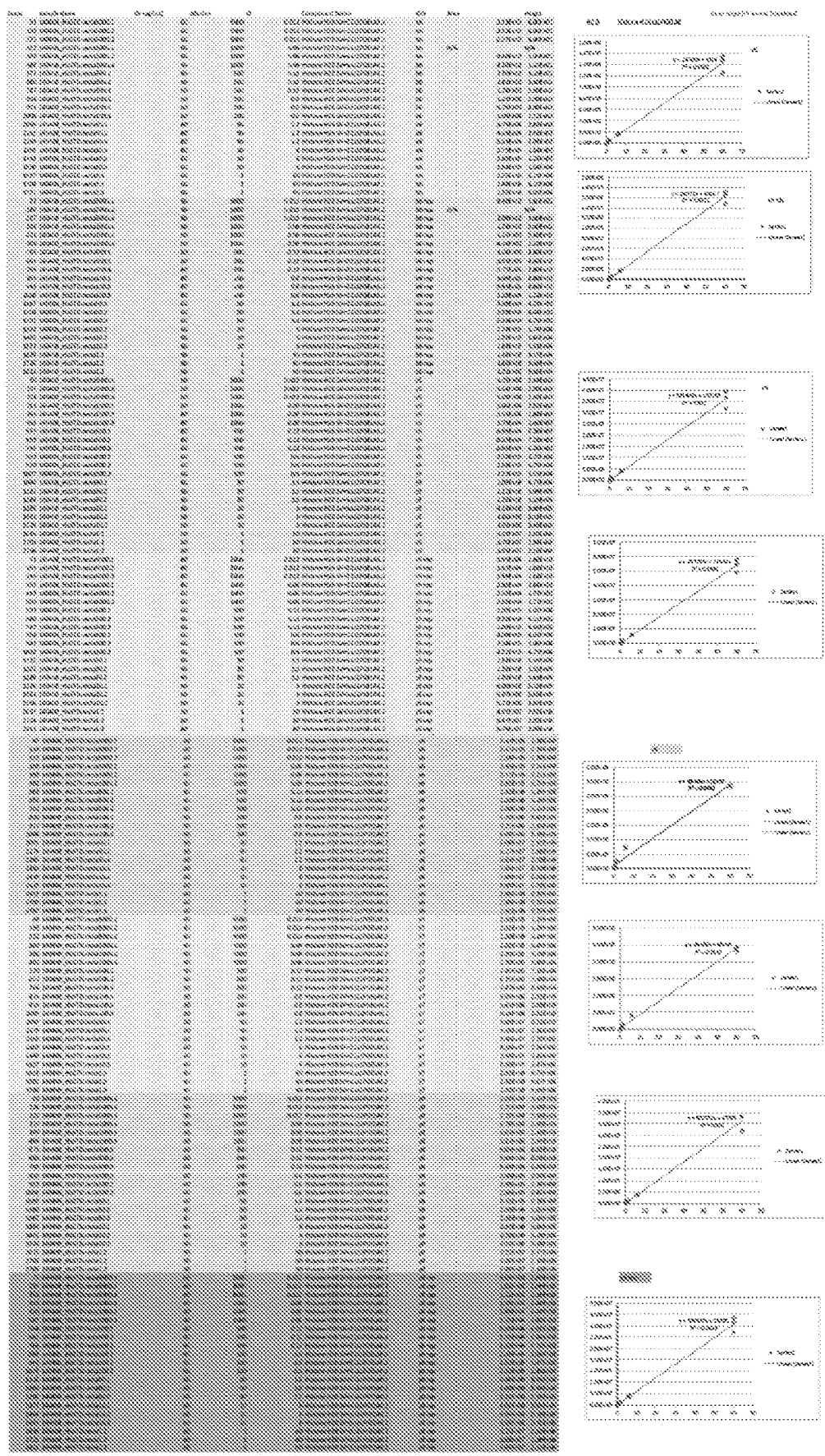
FIG. 9. Response curves for peptide STELLIR for H3. The concentration of light peptide was varied between 0.012 ug/mL to 60 ug/mL and measured relative to the heavy peptide signal. The graphs show the linear regression between area form MS spectrum to peptide concentration for different transitions.

To achieve reliable relative quantification of peptides in complex matrices, the targeted proteomic assay must be analytically characterized with respect to its specificity, linear range, precision, and repeatability. For blood circulating histones quantification, specificity, linear range, precision, and repeatability are mandatory requirements, therefore we checked in our experimental condition the linearity of peptide LLLPGELAK for histone H2B and peptide STELLIR for H3. In FIG. 8 and FIG. 9 we show the linearity of peptide LLLPGELAK for histone H2B and peptide STELLIR for H3, respectively, considering different transitions for each peptide concentration tested.

The results thus demonstrate that the detected concentration of each peptide is above the limit of quantification of the assay and within the linear range of the assay. In fact, peptide LLLPGELAK for histone H2B and peptide STELLIR for H3 showed a good linear range, good sensitivity and specificity. It is noted, that in the context of the present invention "Limit of Quantification" is understood as the lower limit of quantification and refers to the lowest concentration of the analyte at which quantitative measurements can be made. The upper limit of quantification describes the highest concentration of analyte above which the signal departs from linearity. These two limits of quantification define the linear range of the assay.

In addition and as shown in the examples, a total of seventeen patients with clinical diagnosis of SS at admission in a medical ICU were analyzed. Table 1 shows the clinical characteristics of patients. Blood samples were collected from said ICU patients and from healthy subjects in EDTA tubes. Each sample was centrifuged at 2,500 rpm for 10 minutes at room temperature (RT) to separate plasma and then aliquots were stored at −80° C. until their use in MRM-MS experiments. MRM experiments were performed as described in the examples included herein. H2B and H3 histone levels were estimated based on the average ratio obtained for LLPGELAK and STELLIR peptides. Final concentration of H2B and H3 in ng/mL was deduced from relative molecular mass (Mr) values of the targeted proteins (Mr 13.906 Da and 15.404 Da for H2B and H3 respectively).

Figure 2A:
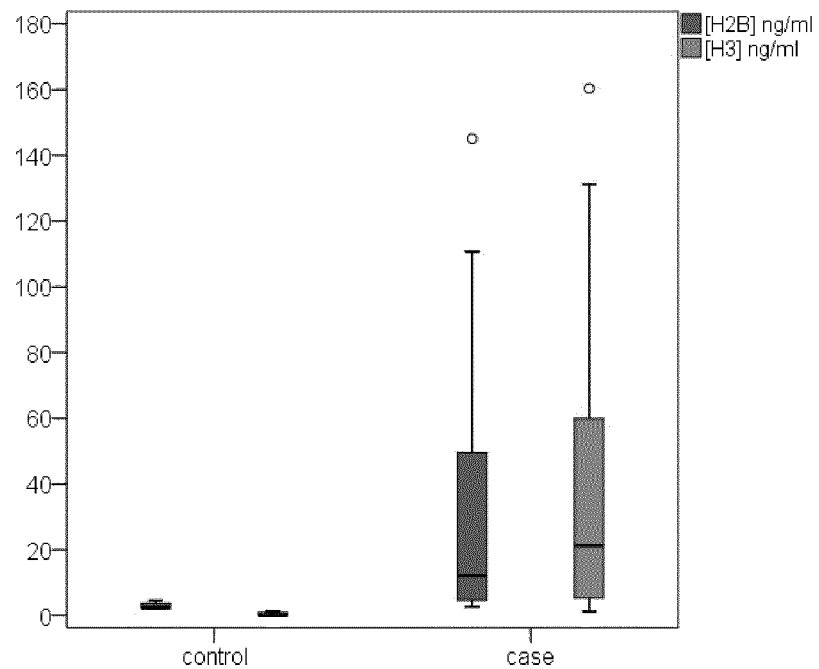
FIG. 2. Box plots showing the level of histones H2B and H3 detected in plasma. A) Box plot representing H2B and H3 levels in healthy subjects versus septic shock patients with bacteremia; B) Box plots representing H2B and H3 levels from survivors and non-survivor SS patients. Boxes denote interquartile ranges, lines denote median, and whiskers denote $10^{th}$ and $90^{th}$ percentiles. Levels are expressed as ng/mL of H2B or H3 in plasma.

For histone H2B the mean level found in controls, healthy subjects, was 204.48 ng/mL (95% CI 25.31-283.66), and in patients it increased up to 1,736.91 ng/mL (95% CI 555.34-2918.47). The differences observed were statistically significant ($p=0.014$), being higher for histone H3 where the mean levels were 23.50 ng/mL (95% CI −3.97-50.98) for controls and 2,040.79 ng/mL (95% CI 756.58-3325.01) for patients ($p=0.004$) (FIG. 2A).

The levels of histones positively correlated with significant correlation coefficients in both groups (Spearman coefficient $r=0.848$, $p=0.002$ for controls and $r=0.827$, $p<0.0001$ for patients).

Figure 2B:
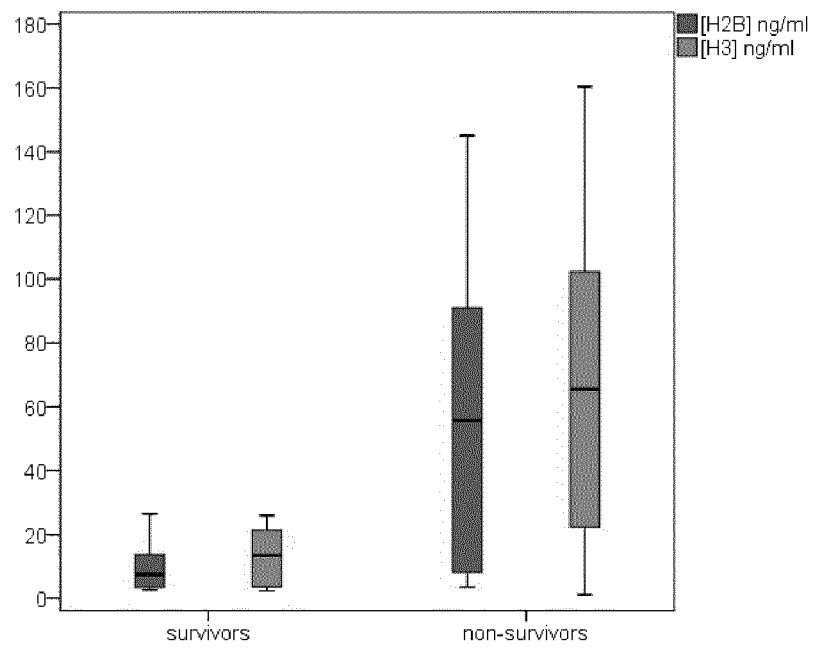

For those patients surviving, the mean level of both histones within the first 24 hours at ICU was significantly low in comparison with non-survivors (FIG. 2B), being the values up to five times lower in comparison with the levels detected in non-survivors. For the histone H2B the mean level was 607.00 ng/mL (95% CI 204.20-1,009.82) in survivors and 3,008.05 ng/mL (95% CI 603.94-5,412.15) in non-survivors ($p=0.046$), and the same proportional differences were observed regarding the levels of histone H3, being the mean values observed 740.70 ng/mL (CI 95% 311.16-1170.23) for survivors and 3,503.41 ng/mL (CI 95% 955.95-6,050.86) for non-survivors ($p=0.036$).

In addition and as shown in the examples, a ROC curve analysis performed to evaluate the diagnostic power of the levels of histones H2B and H3 revealed that both could serve as valuable biomarkers to distinguish septic shock cases from healthy controls. AUCs (area under the ROC curves), standard error, confidence interval (CI), optimal concentration cutoff value, sensitivity and specify for each histone are shown in Table 2.

Although the AUCs for both histones are similar, and the levels of both biomarkers were significantly different between healthy controls and patients, histone H3 showed higher values for sensitivity and specificity regarding diagnosis. For this biomarker, with a concentration of 86.36 ng/mL as optimal cutoff value, the values of sensitivity and specificity of the method were 94.1% and 90.0%, respectively.

Figure 3A:
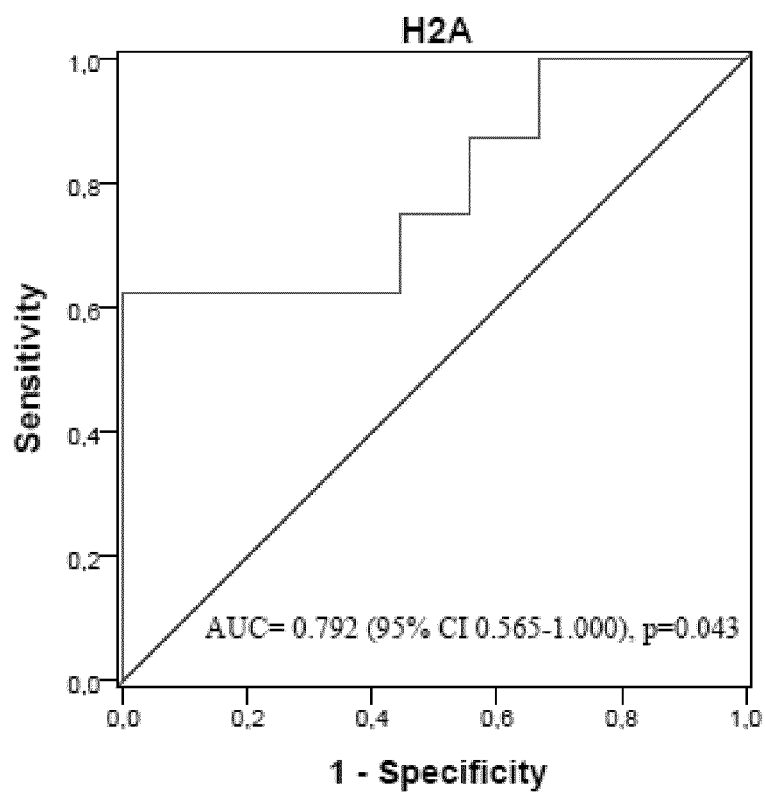
FIG. 3. Receiver Operating Characteristic (ROC) curve for histone H2B (3A) and H3 (3B) for discrimination between survivor and non-survivor SS patients. ROC curve based on the MRM-MS quantification of H2B and H3 levels.
Figure 3B:
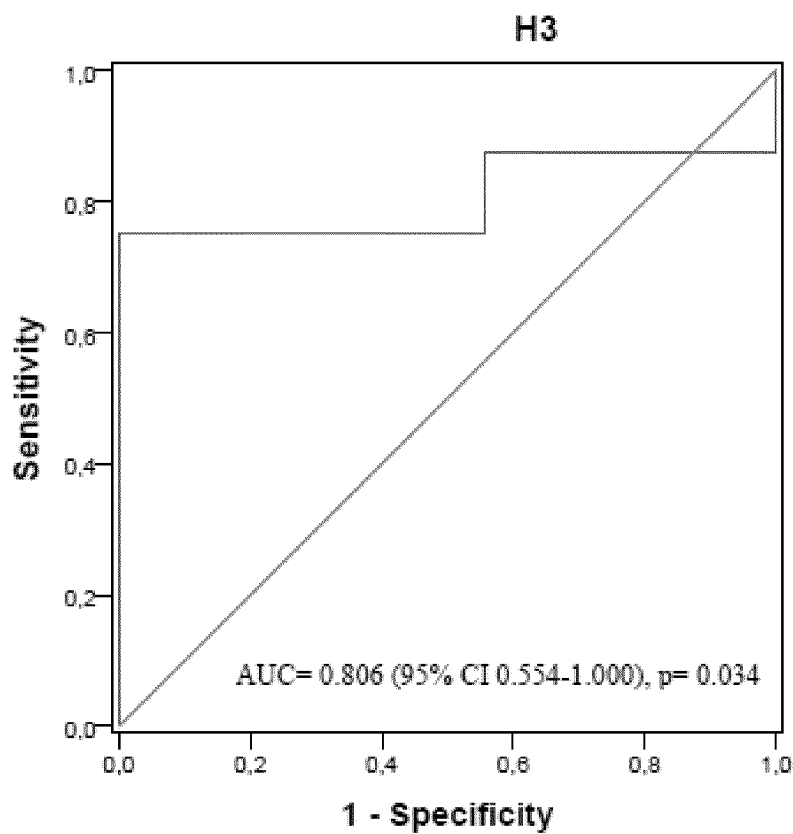

Furthermore, to examine the potential use of histones in plasma as biomarkers for septic shock prognosis, we built the corresponding ROC curve for each histone. We selected just the cases and calculated biomarker parameters: optimal cutoff value, sensitivity and specificity to discriminate between survivors and non-survivors (FIG. 3). Again, histone H3 classified better than histone H2B for prognosis. The sensitivity value was higher for histone H3 (Sensitivity=75.0%, Specificity=88.9%, Cutoff value=1348.13 ng/mL) than for histone H2B (Sensitivity=62.5%, Specificity=88.9%, Cutoff value=1426.38 ng/mL), with similar cutoff values. Therefore, it is thus clear from the results shown herein that both, the levels of histones H2B and H3 in blood, serum or plasma, could serve as valuable biomarkers to distinguish septic shock cases from healthy controls and to discriminate between survivors and non-survivors.

Consequently, a first aspect of the present invention refers to a mass spectrometry-based method for diagnosing or detecting sepsis or septic shock in a human subject comprising the steps of: measuring the level or concentration of at least circulating histones H3 and/or H2B in one or more biological samples consisting of blood, serum or plasma isolated from the subject by using a mass spectrometer; and comparing the level or concentration of said circulating histones from the one or more biological samples of the subject suspected of suffering from sepsis or septic shock with a reference value or with the level or concentration of said circulating histones from a biological sample consisting of blood, serum or plasma of a normal subject, wherein the normal subject is a healthy subject not suffering from sepsis or septic shock, and wherein an increase in the level or concentration of at least circulating histones H3 and/or H2B, is indicative of sepsis or septic shock.

Preferably, the specific concentration range of plasma histones H2B and/or H3 to be used as first triage criteria when patients arrive to ICU, and also become a valuable diagnostic biomarker of sepsis or septic shock, is a range wherein the concentration levels of circulating histone H2B in plasma are above 212.03 ng/ml and/or the concentration levels of circulating histone H3 in plasma are above 86.36 ng/ml. If the concentration levels of H2B or H3 in plasma are beyond any of said values, this is indicative of sepsis or septic shock.

Preferably, the mass spectrometer is a triple quadrupole/ linear ion trap mass spectrometer, preferably equipped with a chromatographic system, more preferably equipped with a nanoLC chromatographic system. Preferably, the mass spectrometry-based method for diagnosing or detecting sepsis or septic shock in a human subject according to the first aspect of the invention or to any of its preferred embodiments, the level or concentration of circulating histone H3 is equivalent to the amount of peptide SEQ ID NO 1 (STELLIR). In this sense, to measure the level or concentration of circulating histone H3 in the biological sample, the averaged ratio, understood as the ratio signal peptide of interest/signal peptide spike-In, of SEQ ID NO 1 is obtained. For the same reasons, to measure the level or concentration of circulating histone H2B in the biological sample, the averaged ratio of SEQ ID NO 2 (LLLPGELAK) is obtained. More preferably, selected peptide sequences (STELLIR for H3; LLLPGE-LAK for H2B) can be preferably prepared as SpikeTidesTM_TQ (heavy-isotope labeled such as Arg: $^{13}C6$, $^{15}N4$; Lys: Arg: $^{13}C6$, $^{15}N2$) (JPT Peptide Technologies, Berlin, Germany) for absolute quantification of circulating histone H3 and/or H2B in the method according to the first aspect of the invention or to any of its preferred embodiments.

In another preferred embodiment of the first aspect of the invention, the reference value for histone H3 is 86.36 ng/mL, wherein an increase of at least 1.5 fold, preferably of at least 2, of at least 3, of at least 4, of at least 5, of at least 6, of at least 7, of at least 8, of at least 9, of at least 10, of at least 15, of at least 20, of at least 30, of at least 40, of at least 50, of at least 60, of at least 70, of at least 80, of at least 90 or of at least 100, is indicative of sepsis or septic shock.

In another preferred embodiment of the first aspect of the invention, the reference value for histone H2B is 212.03 ng/mL, wherein an increase of at least 1.5, of at least 2, of at least 3, of at least 4, of at least 5, of at least 6, of at least 7, of at least 8, of at least 9, of at least 10, of at least 15, of at least 20, of at least 30, of at least 40, of at least 50, of at least 60, of at least 70, of at least 80, of at least 90 or of at least 100, is indicative of septic shock.

In another preferred embodiment of the first aspect of the invention or of any of its preferred embodiments, the method comprises the steps of: measuring the level or concentration of at least circulating histones H3 and H2B in one or more biological samples consisting of blood, serum or plasma isolated from the subject by using a mass spectrometer; and comparing the level or concentration of said circulating histones from the one or more biological samples of the subject suspected of suffering from septic shock with a reference value or with the level or concentration of said circulating histones from a biological sample consisting of blood, serum or plasma of a normal subject, wherein the normal subject is a healthy subject not suffering from septic shock, and wherein an increased in the level or concentration of at least circulating histones H3 and H2B, is indicative of septic shock.

A second aspect of the invention refers to a mass spectrometry-based method for predicting (prognosticating) the clinical evolution of sepsis or septic shock in a human subject suffering from sepsis or septic shock, comprising the steps of: measuring the level or concentration of at least circulating histones H3 and/or H2B in one or more biological samples consisting of blood, serum or plasma isolated from the subject by using a mass spectrometer; and comparing the level or concentration of said circulating histones from the one or more biological samples of the subject suffering from sepsis or septic shock with a reference value, wherein an increased in the level or concentration of at least circulating histones H3 and/or H2B is indicative of a negative clinical evolution, and wherein the clinical evolution refers to the overall survival of the patient.

In the context of the present invention "overall survival" (OS) is understood as the length of time from either the date of diagnosis or the start of treatment for a disease that patients diagnosed with the disease are still alive.

In the context of the present invention "Negative clinical evolution" is understood as negative daily progression of the clinical condition over the first week of sepsis or septic shock with a bad or refractory response to the treatment with mortality outcome.

Preferably, the specific concentration range of plasma histones H2B and/or H3 to be used as first triage criteria when patients arrive to ICU, and also become a valuable prognostic biomarker of sepsis or septic shock, is a range wherein the concentration levels of circulating histone H2B in plasma are above 1426.38 ng/ml and/or the concentration levels of circulating histone H3 in plasma are above 1348.13 ng/ml. If the concentration levels of H2B or H3 in plasma are beyond any of said values, this is indicative of a negative clinical evolution, wherein the clinical evolution refers to the overall survival of the patient.

Preferably, the mass spectrometer is a triple quadrupole/ linear ion trap mass spectrometer equipped with a chromatographic system, more preferably equipped with a nanoLC chromatographic system. Preferably, the mass spectrometry-based method for predicting (prognosticating) the clinical evolution of septic shock in a human subject suffering from septic shock according to the second aspect of the invention or to any of its preferred embodiments, the level or concentration of circulating histone H3 is equivalent to the amount of peptide SEQ ID NO 1 (STELLIR). In this sense, to measure the level or concentration of circulating histone H3 in the biological sample, the averaged ratio of SEQ ID NO 1 is obtained. For the same reasons, to measure the level or concentration of circulating histone H2B in the biological sample, the averaged ratio of SEQ ID NO 2 is obtained. More preferably, selected peptide sequences (STELLIR for H3; LLLPGELAK for H2B) can be preferably prepared as SpikeTidesTM_TQ (heavy-isotope labeled such as Arg: $^{13}C6$, $^{15}N4$; Lys: Arg: $^{13}C6$, $^{15}N2$) (JPT Peptide Technologies, Berlin, Germany) for absolute quantification of circulating histone H3 and/or H2B in the method according to the first aspect of the invention or to any of its preferred embodiments.

In another preferred embodiment of the second aspect of the invention, the reference value for histone H3 is 1,348.13 ng/mL, wherein an increase of at least 1.5 fold, preferably of at least 2, of at least 3, of at least 4, of at least 5, of at least 6, of at least 7, of at least 8, of at least 9, of at least 10, of at least 15, of at least 20, of at least 30, of at least 40, of at least 50, of at least 60, of at least 70, of at least 80, of at least 90 or of at least 100, is indicative of a negative clinical evolution.

In another preferred embodiment of the first aspect of the invention, the reference value for histone H2B is 1,426.38 ng/mL, wherein an increase of at least 1.5 fold, preferably of at least 2, of at least 3, of at least 4, of at least 5, of at least 6, of at least 7, of at least 8, of at least 9, of at least 10, of at least 15, of at least 20, of at least 30, of at least 40, of at least 50, of at least 60, of at least 70, of at least 80, of at least 90 or of at least 100, is indicative of a negative clinical evolution.

In another preferred embodiment of the second aspect of the invention or of any of its preferred embodiments, the method comprises the steps of: measuring the level or concentration of at least circulating histones H3 and H2B in one or more biological samples consisting of blood, serum or plasma isolated from the subject by using a mass spectrometer; and comparing the level or concentration of said circulating histones from the one or more biological samples of the subject suffering from septic shock with a control value, wherein an increased in the level or concentration of at least circulating histones H3 and H2B, is indicative of a negative clinical evolution.

A third aspect of the present invention refers to a kit or device suitable for diagnosing or detecting sepsis or septic shock in a human subject and/or for predicting (prognosticating) the clinical evolution of sepsis or septic shock in a human subject, which comprises: a peptide of SEQ ID NO 1 and/or a peptide of SEQ ID NO 2, wherein these peptides are preferably synthesized with at least one or more heavy amino acids and wherein said peptides are preferably label in the c-terminal amino acid residue with a tag.

In the context of the present invention, the term "tag" is understood as stable isotope labelled amino acids which share the same physiochemical properties and the same chemical activity with their non-labelled amino acids counterparts. Tags can also be a small chemical modification which is cleaved during trypsin or other proteases treatment previous MS experiments. Tags linked to proteotypic peptides are used for peptide quantification in targeted MS experiments.

In the context of the present invention, the term "heavy amino acids" refers to isotopic atoms which are incorporated into the tag containing heavy atoms for example $^{13}C$, $^{15}N$, $^{17}O$ and/or $^{34}S$, which can be distinguished by MS.

In the context of the present invention, the term "synthesized with at least one or more heavy amino acids" is understood as the "Tag" containing at least one or more heavy atoms $^{13}C$, $^{15}N$, $^{17}O$ and/or $^{34}S$ in the Spike-In amino acids sequence corresponding to SEQ ID NO 1 and SEQ ID NO 2.

In a preferred embodiment of the third aspect of the invention, the kit comprises a peptide of SEQ ID NO 1 and a peptide of SEQ ID NO 2, wherein these peptides are preferably synthesized with at least one or more heavy amino acids and wherein said peptides are preferably label in the c-terminal amino acid residue with a tag.

In another preferred embodiment of the third aspect of the invention, the kit may comprise a collection of (diluted or lyophilized) peptides corresponding to SEQ ID NO 1 and SEQ ID NO 2 which have an isotope tag. The kit may also contain instructions indicating how the materials within the kit may be used.

Optionally (Additionally), the kit can include cleaving enzymes such as trypsin, chymotrypsin, pepsin, papain pepsin, papain, *Staphylococcus aureus* (V8) protease, Sub-maxillaris protease, bromelain, thermolysin, aspartate endopeptidase. The kit can also include a chemical reagent such as CNBr, acid or other chemical reagents for chemical generation of protein derived polypeptides.

Optionally, microwave-assisted digestion could be used during trypsin treatments to accelerate the formation of tryptic peptides (P Muralidhar Reddy, et al. Digestion Completeness of Microwave-Assisted and Conventional Trypsin-Catalyzed Reactions. Journal of the American Society for Mass Spectrometry. Volume 21, Issue 3, March 2010, Pages 421-424). The kit could contain trypsin and special microwave-assisted digestion protocol for SEQ ID NO 1 and SEQ ID NO 2 optimal analysis.

A fourth aspect of the invention refers to the in vitro use of the kit as defined in the third aspect of the invention or in any of its preferred embodiments, for diagnosing or detecting septic shock in a human subject or for predicting (prognosticating) the clinical evolution of septic shock in a human subject.

A fifth aspect of the invention refers to a computer program product directly loadable into the internal memory of a digital computer, comprising software code portions for performing the steps of comparing the level or concentration of the circulating histones from the one or more biological samples of the subject suffering from septic shock with a control value and providing a risk of suffering from SS or a risk for a negative clinical evolution of the subject, when said product is run on a computer.

In addition, and as shown in example 2 of the present specification, the present invention also refers, in a sixth aspect of the invention, to a method for the differential diagnosis of sepsis from septic shock in a human subject suspected of suffering from any of these pathologies, wherein the method comprises the steps of: measuring the level or concentration of at least circulating histones H3 and/or H2B in one or more biological samples consisting of blood, serum or plasma isolated from the subject by using a mass spectrometer; and comparing the level or concentration of said circulating histones from the one or more biological samples of the subject suspected of suffering from sepsis or septic shock with a reference value, wherein an increased in the level or concentration of at least circulating histone H2B is indicative of septic shock.

In a preferred embodiment of the six aspect of the invention, the level or concentration of circulating histone H3 is equivalent to the amount of peptide SEQ ID NO 1 (STELLIR). In this sense, to measure the level or concentration of circulating histone H3 in the biological sample, the averaged ratio of SEQ ID NO 1 is obtained. For the same reasons, to measure the level or concentration of circulating histone H2B in the biological sample, the averaged ratio of SEQ ID NO 2 is obtained. More preferably, selected peptide sequences (STELLIR for H3; LLLPGELAK for H2B) can be preferably prepared as SpikeTidesTM_TQ (heavy-isotope labeled such as Arg: $^{13}C6$, $^{15}N4$; Lys: Arg: $^{13}C6$, $^{15}N2$) (JPT Peptide Technologies, Berlin, Germany) for absolute quantification of circulating histone H3 and/or H2B.

In another preferred embodiment of the six aspect of the invention, the mass spectrometer is a triple quadrupole/linear ion trap mass spectrometer equipped with a chromatographic system, more preferably equipped with a nanoLC chromatographic system.

A seventh aspect of the present invention refers to an in vitro use of a kit or the differential diagnosis of sepsis from septic shock in a human subject suspected of suffering from any of these pathologies, which comprises: a peptide of SEQ ID NO 1 and/or a peptide of SEQ ID NO 2, wherein these peptides are preferably synthesized with at least one or more heavy amino acids and wherein said peptides are preferably label in the c-terminal amino acid residue with a tag. In another preferred embodiment of the third aspect of the invention, the kit may comprise a collection of (diluted or lyophilized) peptides corresponding to SEQ ID NO 1 and SEQ ID NO 2 which have an isotope tag. The kit may also contain instructions indicating how the materials within the kit may be used. Optionally (Additionally), the kit can include cleaving enzymes such as trypsin, chymotrypsin, pepsin, papain pepsin, papain, *Staphylococcus aureus* (V8) protease, Submaxillaris protease, bromelain, thermolysin, aspartate endopeptidase. The kit can also include a chemical reagent such as CNBr, acid or other chemical reagents for chemical generation of protein derived polypeptides.

Optionally, microwave-assisted digestion could be used during trypsin treatments to accelerate the formation of tryptic peptides (P Muralidhar Reddy, et al. Digestion Completeness of Microwave-Assisted and Conventional Trypsin-Catalyzed Reactions. Journal of the American Society for Mass Spectrometry. Volume 21, Issue 3, March 2010, Pages 421-424). The kit could contain trypsin and special microwave-assisted digestion protocol for SEQ ID NO 1 and/or SEQ ID NO 2 optimal analysis.

An eighth aspect of the invention refers to a computer program product directly loadable into the internal memory of a digital computer, comprising software code portions for performing the steps of comparing the level or concentration of the circulating histones from the one or more biological samples of the subject suffering from septic shock with a reference value and providing a differential diagnosis of sepsis from septic shock in a human subject suspected of suffering from any of these pathologies, when said product is run on a computer.

The following examples merely illustrate the present invention but do not limit the same.

EXAMPLES

Material and Methods
Patient and Control Subjects Selection

A total of seventeen patients with clinical diagnosis of SS at admission in a medical ICU of the Clinical University Hospital of Valencia (HCUV) (Valencia, Spain), and subsequently confirmed bacteremia (microbiological blood positive culture at 48 hours) were included in this study. Exclusion criteria were: i) patients with a life expectancy lower than 24 hours; ii) patients outside the age range between 18 and 85 years; iii) patients with an active neoplastic process or treated with antioxidants; iv) patients with a stay longer than 24 hours in the hospital ward, or in another hospital; v) surgical patients, or those patients in a post-cardiopulmonary resuscitation state, or suspected viral infection, as well as pregnant women and patients who did not grant their consent, were also excluded. Patients and controls were enrolled in the study after approval by the Biomedical Research Ethics Committee (CEIC) of HCUV and the IBSP-CV Biobank (Biobank for Biomedical Research and Public Health in the Valencian Community, Spain).

Blood Collection

Blood samples were collected from ICU patients and healthy subjects in EDTA tubes. Each sample was centrifuged at 2,500 rpm for 10 minutes at room temperature (RT) to separate plasma and then aliquots were stored at −80° C. until their use in MRM-MS experiments.

Linearity Assessment for Spiked-in Peptides

First, commercial purified human histones H3 and H2B (EpiGex, Illkirch, France) were trypsinized and analyzed using LC-MS/MS_DDA in a 5600 triple TOF (ABSciex, Framingham, Mass., USA) to identify those unequivocal peptides with good signal. From the different fragmentation spectra (MSMS) peptide precursors and fragment ion masses were selected for H3 and H2B to be analyzed for MRM-MS. MRM parameters were optimized in a 5500 QTRAP instrument (ABSciex) by the MRM-PILOT software (AB Sciex), determining the declustering potential (DP) for every peptide and dwell time (DT) and collision energy for each transition (CE). Afterwards, histone-derived peptides with high number of detectable transitions, high sensitivity and high linear dinamic range were chosen to perform MRM-MS experiments. Selected peptide sequences (STELLIR for H3; LLLPGELAK for H2B) were prepared as SpikeTidesTM_TQ (heavy-isotope labeled; Arg: $^{13}C6$, $^{15}N4$; Lys: Arg: $^{13}C6$, $^{15}N2$) (JPT Peptide Technologies, Berlin, Germany) for absolute quantification.

Sample Preparation

Protein content was measured by the Bradford method (Bio-Rad, Hercules, Calif., USA). 1 µL of plasma (not depleted) was diluted in 20 µL of a 1:1 ammonium bicarbonate 0.1/trifluoroethanol solution. For each 1 µg of protein content, 300 fmols of both heavy peptides were added. Then, cysteine residues were reduced by addition of 10 mM D-L-dithiothreitol at 56° C. for 30 min. Sulfhydryl groups were alkylated with 14 mM iodoacetamide in the dark at RT for 30 min. The excess was neutralized with 10 mM D-L-dithiothreitol in 50 mM ammonium bicarbonate in a final volume of 100 µL during 30 min at RT. Sample was subjected to trypsin digestion with 1 µg of sequencing grade-modified trypsin (TCPK Trypsin-ABSciex) overnight at 37° C. The reaction was stopped with trifluoroacetic acid (TFA) at a final concentration of 1%. Samples were dried using speedvac and resuspended in 50 µL of TFA (0.1%). Peptides were concentrated and purified using ZipTip C18 Tips (Merck Millipore, Darmstadt, Germany). Finally, samples were diluted in 2% acetonitrile (CAN), 0.1% formic acid (FA) for injection.

MRM-MS

MRM experiments were performed on a 5500 QTRAP hybrid triple quadrupole/linear ion trap mass spectrometer (ABSciex) equipped with an Eksigent 1 D+plus nanoLC chromatographic system. Tryptic digest (1 µg of protein and 300 fmol of each Spike-In peptide) was injected onto a NanoLC trap column, 3µ C18-CL (Eksigent, Dublin, Calif., USA), and then separated by RP-HPLC on an analytic nanoLC column 3p C18-CL, 15 cm (Eksigent). Chromatography was performed with solvent A (0.1% FA) and solvent B (100% ACN, 0.1% FA) as mobile phase, using a linear gradient (70 minutes from 2% B to 50% B) at a 300 nl/min flow rate. MRM data were acquired in a positive mode with a spray voltage of 2800V, curtain gas: 20 psi, ion source gas: 20 psi, interface heater temperature: (IHT) 150° C., DP: 80, entrance potential: 10, exit potential: (EXP) 15, and a pause time of 3 ms. Collision Energy (CE) was 26V and 23V for LLLPGELAK-LLLPGELA[K] and STELLIR-STELLI[R], respectively. Transitions (9 for STELLIR and STELLI[R]; and 12 for LLLPGELAK and LLLPGELA[K]) were monitored using Unit Resolution in both Q1 and Q3 quadrupoles, and 40 ms of dwell time for each one. Data analysis was performed using Analyst® 1.5.2 and MultiQuant® 2.0.2 softwares (ABsciex). The area ratio (light/heavy) for all transitions was calculated, and the average area ratio was used for statistical analysis.

To calculate H2B and H3 histone levels we used the average ratio obtained for LLLPGELAK and STELLIR. Final concentration of H2B and H3 in mg/mL was deduced form relative molecular mass (Mr) values of the targeted proteins (Mr 13.906 Da and 15.404 Da for H2B and H3 respectively).

Statistical Analysis

Sociodemographic and clinical baseline characteristics of participants were compared between groups using the Student's test for age and chi-squared test for gender. Concentration of histones H2B and H3 were compared using parametric and non-parametric tests such as Student, ANOVA and Mann-Whitney U. Correlation between H2B and H3 levels, Acute Physiology and Chronic Health Evaluation II (APACHE II) and Sequential Organ Failure Assessment (SOFA) scores, lactate and prothrombin time were assessed using Spearman's correlations.

The value for the levels of histones H2B and H3 as biomarkers for diagnosis and prognosis of SS was carried-out by Receiver Operating Characteristic (ROC) curves analysis.

P-values <0.05 were regarded as statistically significant. All the analysis was conducted using SPSS v. 20 (IBM Corporation, Armonk, N.Y., USA).

Example 1. Results

General Description of the Cohorts

A total of seventeen patients with clinical diagnosis of SS at admission in a medical ICU were analyzed. The median age was 67 years (37-85) and male patients accounted for 67% of cases. A median APACHE II score was 25 (14-44) and SOFA score median value was 10 (3-19).

TABLE 1 shows the clinical characteristics of patients.
Clinical features of patients with bacteriemic-septic shock

|  | SURVIVORS (n = 9) | NON-SURVIVORS (n = 8) | p value |
|---|---|---|---|
| Age (years) (Mean ± SD) | 66 ± 12 | 63 ± 14 | 0.72 |
| Male gender (%) | 7 (78) | 5 (62) | 0.43 |
| APACHE II score (Mean ± SD) | 21 ± 4 | 29 ± 10 | 0.05 |
| Charlson Index > 3 (%) | 4 (44) | 4 (50) | 0.6 |
| SOFA score $1^{st\ day}$ (Mean ± SD) | 9 ± 2 | 11 ± 5 | 0.5 |
| Antibiotic two weeks previous to admission (%) | 2 (22) | 1 (12.5) | 0.54 |
| Hospital admission in the previous three weeks | 2 (22) | 3 (37) | 0.53 |
| Infection source (%) | | | |
| Abdominal/urologic | 8 (88.8) | 4 (50) | |
| Respiratory | 0 | 2 (25) | |
| SSTI/bone infection | 0 | 2 (25) | |
| Unknown | 1 (11) | 0 | 0.09 |
| Microorganisms (%) | | | |
| MDR[a] | 0 | 2 (25) | |
| Non-MDR[b] | 9 (100) | 5 (62.5) | |
| *Candida* spp. | 0 | 1 (12.5) | 0.17 |
| Organ support therapy (%) | | | |
| Antimicrobial in first hour | 6 (67) | 4 (50) | 0.48 |
| Corticosteroid therapy | 4 (52) | 6 (75) | 0.42 |
| Crystalloids (mL) (Mean ± SD) | 1,811 ± 382 | 1,850 ± 111 | 0.93 |
| Vasopressor therapy | 9 (100) | 8 (100) | NS |
| RRT | 3 (33) | 7 (87) | 0.03 |
| Mechanical ventilation | 2 (22) | 7 (87) | 0.01 |
| Lactate Clearance[c] | 8 (89) | 3 (37.5) | 0.04 |
| ICU LOS (days) (Median ± SD) | 7 ± 7 | 11 ± 11 | 0.47 |
| Hospital LOS (days) (Median ± SD) | 18 ± 15 | 17 ± 21 | 0.90 |
| White blood cells (Mean ± SD) | 19,464 ± 10,731 | 15,207 ± 12,200 | 0.45 |
| CRP (mg/l) (Mean ± SD) | 288 ± 51 | 279 ± 77 | 0.90 |
| Procalcitonin (ng/mL) (Mean ± SD) | 61 ± 15 | 22 ± 13 | 0.07 |
| Lactate $1^{st\ hour}$ (mmol/l) (Mean ± SD) | 5 ± 3 | 8 ± 6 | 0.10 |
| Lactate $6^{hours}$ (mmol/l) (Mean ± SD)[c] | 3 ± 3 | 6.5 ± 4 | 0.05 |
| Glucose (mg/dl) (Mean ± SD) | 142 ± 50 | 210 ± 100 | 0.11 |
| Creatinine (mg/dl) (Mean ± SD) | 2.9 ± 1.5 | 2.5 ± 1.2 | 0.58 |
| PaO2/FiO2 Ratio (Mean ± SD) | 266 ± 103 | 163 ± 69 | 0.03 |
| Prothrombin Time (seconds) (Mean ± SD) | 16.6 ± 2.8 | 20.4 ± 4.7 | 0.05 |
| Platelets count (Mean ± SD) | 145,111 ± 101,160 | 243,875 ± 140,026 | 0.11 |
| Albumin (g/dl) (Mean ± SD) | 2.8 ± 0.2 | 2.6 ± 0.5 | 0.39 |

SD = standard deviation,
APACHE = acute physiology and chronic health evaluation,
SOFA = sequential organ failure assessment,
SSTI = skin and soft tissue infection,
MDR = multidrug resistant microorganisms,
RRT = Renal replacement therapy,
ICU = intensive care unit,
LOS = length of stay
CRP = C-reactive protein,
PaO2/FiO2 Ratio = arterial oxygen partial pressure to fractional inspired oxygen
[a]MDR (Extended Spectrum Betalactamase-producing *Escherichia coli* and Meticilin Resistant *Staphylococcus aureus*)
[b]Non-MDR (*Escherichia coli, Klebsiella pneumoniae, Enterococcus faecalis, Enterococcus faecium, Enterobacter cloacae, Streptococcus mitis* and *Streptococcus pneumoniae*)
[c]Lactate clearance over 10% during the first six hours of hemodynamic resuscitation There were 9 (53%) survivors and 8 (47%) non-survivors. Both groups were similar with respect to demographic characteristics, comorbidities at admission according to the Charlson Index and severity, although non-survivors had a tendency to a higher mean APACHE II score. There were no differences with regard to infection source and identified microorganisms in blood samples between both groups, neither considering multidrug-resistant and gram-analysis criteria.

Initial management was similar in both groups of SS patients. Survivors and non-survivors received intravenous antimicrobial therapy within the first hour of recognition of SS and fluid resuscitation (initial administration of at least 20 mL/kg of intravenous crystalloids for improving hemodynamics in the absence of formal contraindication) in the same level. Subsequently all patients in the survivor group received "adequate" antimicrobial therapy based on definitive blood culture results, while this value was 75% for the non-survivors According to organ support therapy, all patients needed vasoactive drugs at the beginning (considering the SS inclusion criteria) and a patient population higher than 50% was treated with corticosteroids based on a refractory situation in both groups. The mortality of those patients whose lactate levels fell >10% after fluid resuscitation was 27% vs. 83% in those who did not, with an odds ratio (OR) of ICU mortality of 0.4 (IC 0.16-1.06) for patients who clear this metabolite. No difference was observed with respect to the median ICU and hospital lengths of stay between both groups of patients.

Regarding the blood test results of patients on the first day of ICU stay, there were scarce differences between both groups. Inflammatory parameters (white blood cells count, C-reactive protein (CRP) and procalcitonin (PCT) levels) were comparable as well as the first level of lactate reflecting a homogeneous clinical hypoperfusion. Significant differences were observed in lactate levels after six hours of therapy, prothrombin time and arterial oxygen partial pressure to fractional inspired oxygen (PaO2/FiO2) ratio between both groups, showing once again the worse situation and more advanced organ dysfunction in the non-survivors group.

A total of 10 healthy controls were recruited, they were younger and more likely to be males than the cases. The median age of controls was 42 years (20-56) and male controls accounted for 70%.

MRM Analysis of H2B and H3

First, a selection of histone peptides was assayed to choose the best peptides for Spiked-In preparations and posterior MRM-MS measures in blood samples. Peptides LLLPGELAK and STELLIR, derived from tryptic digestion of purified H2B and H3, respectively, were selected upon experimental observations in LC-MS/MS experiments. This is a critical point in order to design MRM assays because different peptides from the same protein can vary widely in their MS response and could produce interferences in plasma samples. The unique peptide sequences we chose exhibited good chromatographic parameters, optimal ionization efficiency and high MS/MS quality, and showed large concentration linearity for the signal (data not shown). Both sequences were used for spiking plasma samples of SS patients and healthy subjects.

FIG. 1 shows the chromatograms with the most intense (as previously defined) MRM signals that track H2B and H3 in plasma samples. Using Multiquant® (ABsciex) for analyzing spiked plasma samples with 300 fmol of LLLPGELAK and STELLIR per 1 µg of protein, we were able to detect peptides with a good signal-to-noise ratio.

Figure 4:
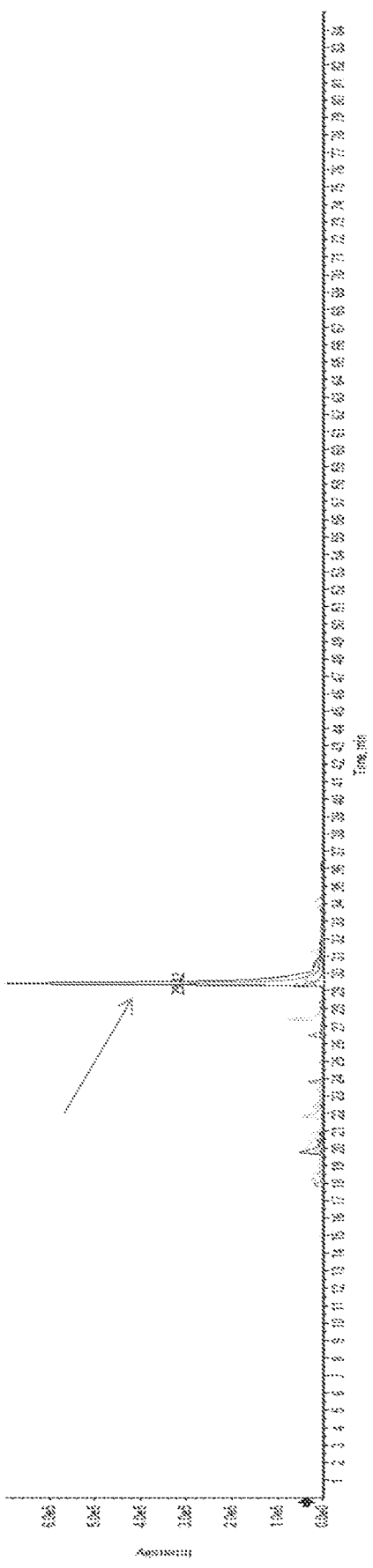
FIG. 4. Nonspecific endogenous multiple reaction monitoring (MRM) signals observed in total chromatograms for A) LLLPGELAK and B) STELLIR. Arrows indicate the peaks assigned to the peptide of interest. No interfering peaks at the elution time of both peptides were found.
Figure 4:
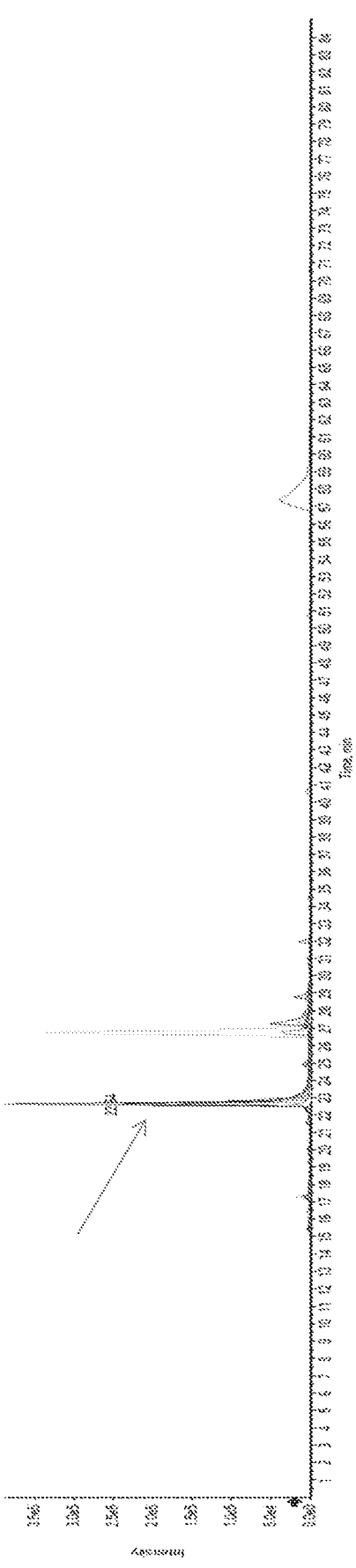

Non interfering peaks at the elution time of both peptides were found (FIG. 4).

Circulating Histones H2B and H3 as Potential Biomarkers for the Diagnosis and Prognosis of SS For histone H2B the mean level found in controls was 204.48 ng/mL (95% CI 25.31-283.66), and in patients it increased up to 1,736.91 ng/mL (95% CI 555.34-2,918.47). The differences observed were statistically significant (p=0.014), being higher for histone H3 where the mean levels were 23.50 ng/mL (95% CI −3.97-50.98) for controls and 2,040.79 ng/mL (95% CI 756.58-3,325.01) for patients (p=0.004) (FIG. 2).

The levels of histones positively correlated with significant correlation coefficients in both groups (Spearman coefficient r=0.848, p=0.002 for controls and r=0.827, p<0.0001 for patients).

For those patients surviving, the mean level of both histones within the first 24 hours at ICU was significantly low in comparison with non-survivors (FIG. 2), being the values up to five times lower in comparison with the levels detected in non-survivors. For the histone H2B the mean level was 607.00 ng/mL (95% CI 204.20-1,009.82) in survivors and 3,008.50 ng/mL (95% CI 603.94-5,412.15) in non-survivors (p=0.046), and the same proportional differences were observed regarding the levels of histone H3, being the mean values observed 740.70 ng/mL (CI 95% 311.16-1170.23) for survivors and 3503.41 ng/mL (CI 95% 955.95-6,050.86) for non-survivors (p=0.036).

Specificity and Sensitivity of Histones H2B and H3 Detected by MRM-MS Method

ROC curve analysis performed to evaluate the diagnostic power of the levels of histones H2B and H3 revealed that both could serve as valuable biomarkers to distinguish septic shock cases from healthy controls. AUCs (area under the ROC curves), standard error, confidence interval (CI), optimal concentration cutoff value, sensitivity and specify for each histone are shown in Table 2.

TABLE 2

ROC curves parameters for histones H2B and H3 levels as biomarkers for diagnosis of septic processes

| Histone | AUC | Standard error | 95% CI | Concentration (ng/mL) optimal cutoff value | P value | Sensitivity (%) | Specificity (%) |
|---|---|---|---|---|---|---|---|
| H2B | 0.865 | 0.069 | 0.730-0.999 | 212.03 | 0.002 | 82.4 | 70.0 |
| H3 | 0.988 | 0.015 | 0.958-1.000 | 86.36 | <0.0001 | 94.1 | 90.0 |

Although the AUCs for both histones are similar, and the levels of both biomarkers were significantly different between healthy controls and patients, histone H3 showed higher values for sensitivity and specificity regarding diagnosis. For this biomarker, with a concentration of 83.36 ng/mL as optimal cutoff value, the values of sensitivity and specificity of the method were 94.1% and 90.0% respectively.

Circulating H2B and H3 and their Potential for Patient Early Outcome.

To examine the potential use of histones in plasma as biomarkers for septic shock prognosis, we built the correspondent ROC curve for each histone. We selected just the cases and calculated biomarker parameters: optimal cutoff value, sensitivity and specificity to discriminate between survivors and non-survivors (FIG. 3). Again, histone H3 classified better than histone H2B for prognosis. The sensitivity value was higher for histone H3 (Sensitivity=75.0%, Specificity=88.9%, Cutoff value=1,348.13 ng/mL) in contrast to histone H2B (Sensitivity=62.5%, Specificity=88.9%, Cutoff value=1,426.38 ng/mL), with similar cutoff values.

Example 2. Differential Diagnosis

A total of 40 samples were analyzed, with the following distribution between the groups included in the study: 11 controls selected at the ICU with no infectious pathologies (controls nonseptic ICU patients), 11 controls selected from healthy general population, 8 cases of sepsis and 10 cases of septic shock.

For histone H2B, the mean levels found in the 40 plasmas were the following (table 2):

| Group | [H2B] ng/mL (CI 95%) |
|---|---|
| Control ICU population | 132.63 (92.68-172.59) |
| Control general population | 108.87 (84.23-133.50) |
| Sepsis | 219.63 (162.05-277.21) |
| Septic shock | 1305.32 (587.42-2023.23) |

Figure 5:
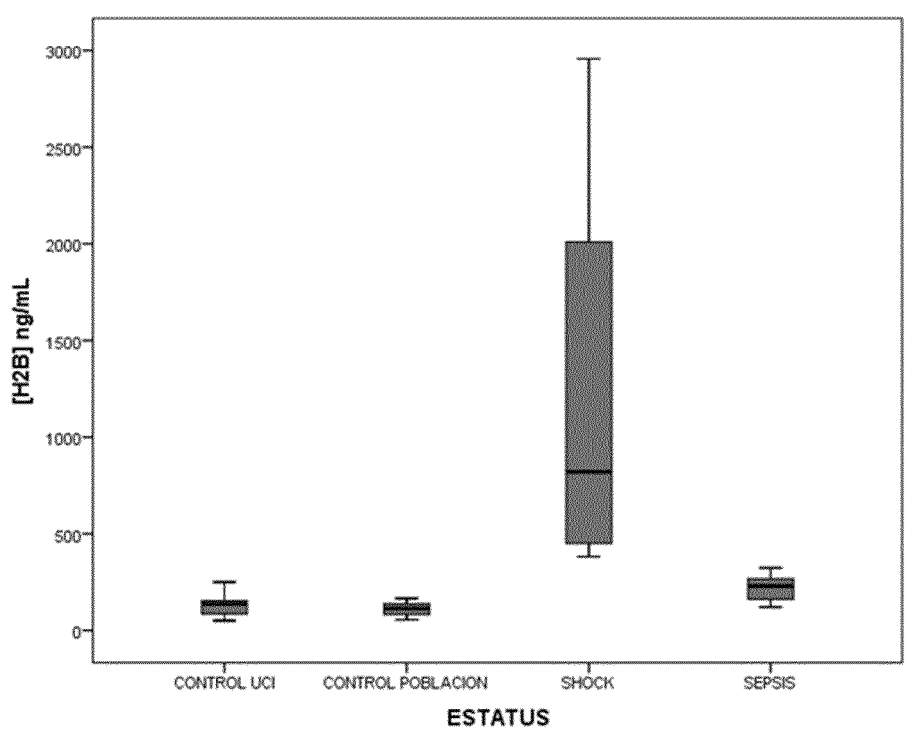
FIG. 5. Levels of circulating histone H2B in plasma from control non-septic ICU (intense care unit) patients and healthy general population, sepsis and septic shock patients. Box and whisker plots represent the H2B levels in the four groups. Boxes denote interquartile ranges, horizontal lines denote medians, and whiskers denote the 10th and 90th percentiles. Levels are expressed as ng/mL of H2B.

The results are shown in FIG. 5, wherein levels of circulating histone H2B in plasma from control (ICU and general population), sepsis and septic shock patients are shown. Box and whisker plots represent the H2B levels in the four groups. Boxes denote interquartile ranges, horizontal lines denote medians, and whiskers denote the 10th and 90th percentiles. Levels are expressed as ng/mL of H2B.

To assess if the differences observed were statistical significant, we performed and ANOVA test (p<0.0001). The post-hoc tests (Scheffé) indicate that these statistical differences were between the septic shock samples and the ICU control group (p<0.0001), the general population control group (p<0.0001), and the sepsis group (p=0.001).

The invention claimed is:

1. A mass spectrometry-based method for measuring the level or concentration of at least circulating histone H3 in one or more biological samples from a first human subject suspected of having sepsis or septic shock, comprising determining the amount of peptide SEQ ID NO 1 (STELLIR) present in the biological sample after trypsin digestion or treatment using a mass spectrometer, wherein the sample is selected from blood, serum and plasma isolated from the subject, and wherein to measure the level or concentration of circulating histone H3 in the biological sample the averaged ratio of SEQ ID NO 1 is obtained, and wherein an increase in the level or concentration of at least circulating histone H3 relative to a reference value or relative to the level or concentration of circulating histone H3 from a corresponding biological sample of a second human subject not suffering from sepsis or septic shock, is indicative that the first human subject is suffering from sepsis or septic shock.

2. The mass spectrometry-based method according to claim 1, wherein the reference value for histone H3 is 86.36 ng/mL, and wherein an increase of at least 1.5 fold is indicative of sepsis or septic shock.

3. The mass-spectrometry-based method of claim 1, wherein the method further comprises measuring the level or concentration of at least circulating histone H2B in the one or more biological samples from the first human subject by using a mass spectrometer, wherein the level or concentration of circulating histone H2B is equivalent to the amount of peptide SEQ ID NO 2 (LLPGELAK), and wherein to measure the level or concentration of circulating histone H2B in the biological sample the averaged ratio of SEQ ID NO 2 is obtained, and wherein an increase in the level or concentration of circulating histone H3 and H2B relative to a reference value or relative to the level or concentration of circulating histone H3 and H2B from the corresponding biological sample of the second human, is indicative that the first human subject is suffering from sepsis or septic shock.

4. The mass spectrometry-based method according to claim 3, wherein the reference value for histone H2B is 212.03 ng/mL, and wherein an increase of at least 1.5 fold is indicative of sepsis or septic shock.

* * * * *